United States Patent
Karnik et al.

(10) Patent No.: US 10,602,981 B2
(45) Date of Patent: Mar. 31, 2020

(54) OPTICAL PRESSURE SENSOR

(71) Applicant: Microsoft Technology Licensing, LLC, Redmond, WA (US)

(72) Inventors: Ryna Karnik, Redmond, WA (US); Hamid Shayesteh-pour, Woodinville, WA (US); Vinod L. Hingorani, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 226 days.

(21) Appl. No.: 14/292,566

(22) Filed: May 30, 2014

(65) Prior Publication Data
US 2015/0342527 A1    Dec. 3, 2015

(51) Int. Cl.
*A61B 5/00* (2006.01)
*A61B 5/024* (2006.01)
*A61B 5/11* (2006.01)

(52) U.S. Cl.
CPC .......... *A61B 5/6843* (2013.01); *A61B 5/0059* (2013.01); *A61B 5/02427* (2013.01); *A61B 5/02438* (2013.01); *A61B 5/1123* (2013.01); *A61B 5/486* (2013.01); *A61B 5/681* (2013.01); *A61B 5/6885* (2013.01); *A61B 5/7214* (2013.01); *A61B 5/7267* (2013.01); *A61B 5/742* (2013.01); *A61B 5/721* (2013.01); *A61B 5/7221* (2013.01); *A61B 2562/0219* (2013.01); *A61B 2562/0247* (2013.01)

(58) Field of Classification Search
None
See application file for complete search history.

(56) References Cited

U.S. PATENT DOCUMENTS

| | | | |
|---|---|---|---|
| 7,470,234 B1 | 12/2008 | Elhag et al. | |
| 8,461,998 B2 | 6/2013 | Ruhs et al. | |
| 9,636,059 B2 * | 5/2017 | Cinbis | A61B 5/1459 |
| 2009/0281435 A1 * | 11/2009 | Ahmed | A61B 5/02416 |
| | | | 600/502 |
| 2010/0109895 A1 | 5/2010 | Rosener | |
| 2010/0113948 A1 | 5/2010 | Yang et al. | |

(Continued)

FOREIGN PATENT DOCUMENTS

| | | |
|---|---|---|
| AT | 413327 B | 2/2006 |
| CN | 102106725 A | 6/2011 |

(Continued)

OTHER PUBLICATIONS

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.

(Continued)

*Primary Examiner* — Katherine L Fernandez
(74) *Attorney, Agent, or Firm* — Alleman Hall Creasman & Tuttle LLP (57) ABSTRACT

A pressure sensor comprises an optical source configured to illuminate the tissue of a user, and an optical sensor configured to measure reflected illumination from the tissue. A compute system is configured to output a pressure between a surface of the optical sensor and the tissue as a function of the measured reflected illumination.

14 Claims, 5 Drawing Sheets

(56) References Cited

U.S. PATENT DOCUMENTS

| | | | |
|---|---|---|---|
| 2011/0050428 A1 | 3/2011 | Istoc | |
| 2011/0098583 A1 | 4/2011 | Pandia et al. | |
| 2012/0041276 A1 | 2/2012 | Doreus et al. | |
| 2012/0078130 A1 | 3/2012 | Ahmed et al. | |
| 2013/0041237 A1* | 2/2013 | Kanayama | A61B 5/14532 600/316 |
| 2013/0044215 A1 | 2/2013 | Rothkopf et al. | |
| 2013/0119255 A1 | 5/2013 | Dickinson et al. | |
| 2013/0253332 A1* | 9/2013 | Hayman | A61B 5/0059 600/476 |
| 2013/0296714 A1* | 11/2013 | Kassim | A61B 5/6898 600/479 |
| 2014/0051941 A1* | 2/2014 | Messerschmidt | A61B 5/6898 600/301 |
| 2014/0073486 A1* | 3/2014 | Ahmed | A61B 5/02405 482/9 |
| 2014/0099614 A1* | 4/2014 | Hu | G09B 19/00 434/236 |
| 2014/0107493 A1* | 4/2014 | Yuen | A61B 5/0205 600/473 |
| 2014/0107497 A1* | 4/2014 | Semler | A61B 5/02405 600/479 |
| 2014/0135594 A1* | 5/2014 | Yuen | A61B 5/6885 600/301 |
| 2014/0275850 A1* | 9/2014 | Venkatraman | A61B 5/0002 600/301 |

FOREIGN PATENT DOCUMENTS

| | | |
|---|---|---|
| CN | 103384493 A | 11/2013 |
| CN | 103549944 A | 2/2014 |

OTHER PUBLICATIONS

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

"Actiwatch Spectrum Plus for Scientific Sleep, Activity, Light Exposure Monitoring", Published on: Jan. 17, 2014 Available at: http://www.medgadget.com/2014/01/actiwatch.html.

Liszewski, Andrew, "Heart Rate Monitoring Glove Based on Plethysmography", Published on: Jun. 7, 2007 Available at: http://www.ohgizmo.com/2007/07/06/heart-rate-monitoring-glove-based-on-plethysmography/.

ISA European Patent Office, International Search Report and Written Opinion Issued in Application No. PCT/US2015/032773, dated Sep. 4, 2015, WIPO, 9 pages.

IPEA European Patent Office, International Preliminary Report on Patentability Issued in Application No. PCT/US2015/032773, dated Aug. 17, 2016, WIPO, 8 Pages.

IPEA European Patent Office, Second Written Opinion issued in PCT Application No. PCT/US2015/032773, dated Apr. 20, 2016, WIPO, 7 pages.

"First Office Action and Search Report Issued in Chinese Patent Application No. 201580026798", dated Nov. 5, 2018, 12 Pages.

"Second Office Action and Search Report Issued in Chinese Patent Application No. 201580026798.X", dated Jul. 2, 2019, 13 Pages.

* cited by examiner

OPTICAL PRESSURE SENSOR

DETAILED DESCRIPTION

The present disclosure is directed to monitoring the pressure between an optical sensor and tissue of a user, and in particular, to determining the pressure based on an optical signal from the optical sensor. In one application, the determined pressure may be used to increase the robustness of an optical heart rate sensor. Additionally or alternatively, the determined pressure may be used as an input to an activity classifier, to adjust characteristics of an optical source, and/or to provide other types of feedback to a user. While described in the context of a wearable computing device, the pressure between an optical sensor and tissue of a user may be used in numerous different applications, and with various different types of sensory-and-logic systems.

A wearable computing device may incorporate an optical heart rate sensor, allowing a user to constantly monitor health factors, such as heart rate, calories burned, response to exertion exercises, heart rate variability, etc. However, the quality of the signal from the optical sensor may be reduced with excessive pressure due to bleaching of the underlying skin and tissue. As such, the optical heart rate sensor may only be accurate within a particular range of pressures. A pressure sensor, such as a resistor or capacitor, may be used to estimate pressure between the wearable computing device and the tissue of the user. However, resistors and capacitors only measure pressure at a specific location. As users have different limb and body profiles, the pressure profile between a wearable computing device and a user will vary by individual. As such, the output of a pressure sensor that is not at the same position as an optical sensor may not track with the pressure at the optical sensor.

According to this disclosure, the output of the optical sensor itself may be used to determine pressure based on changes in reflected illumination. For example, an increase in pressure may correlate to an increase in reflected illumination from an optical source. A decrease in pressure may correlate with a decrease in reflected illumination from the optical source. The optical source may pulse on and off to allow for an assessment of the quantity of ambient light reaching the optical sensor. An increase in ambient light while the optical source is off may indicate the wearable computing device is not being worn. Further, changes in the pressure profile over time may be indicative of a specific physical activity. By determining pressure using the optical sensor output, the accuracy of a heart rate sensor may be increased without requiring an additional pressure sensor to be incorporated into the wearable computing device.

Figure 1A:
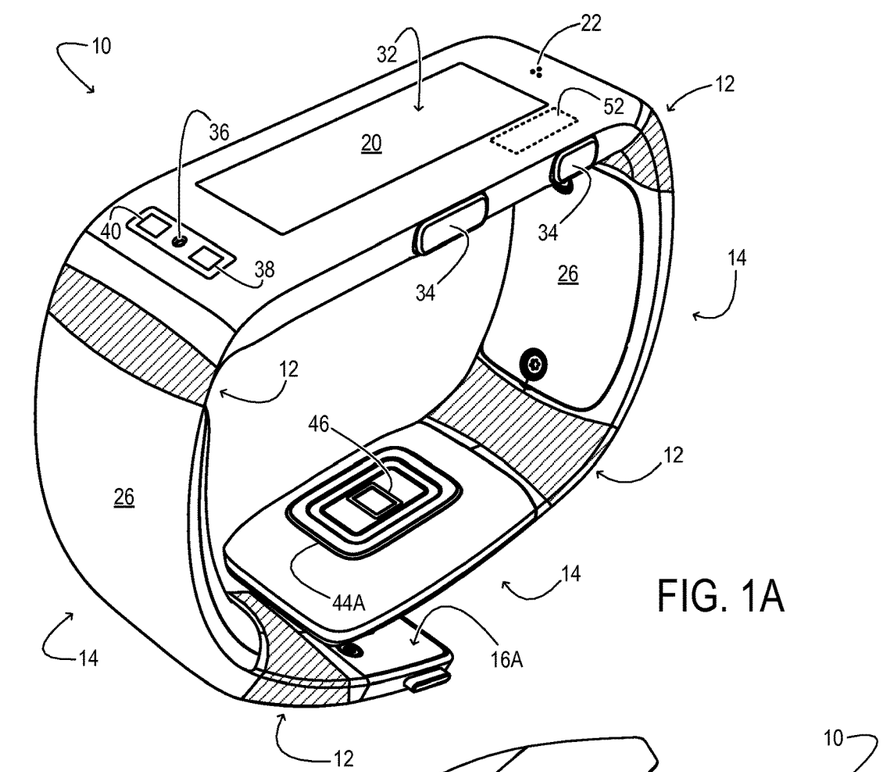
FIGS. 1A and 1B show a wearable electronic device.
Figure 1B:
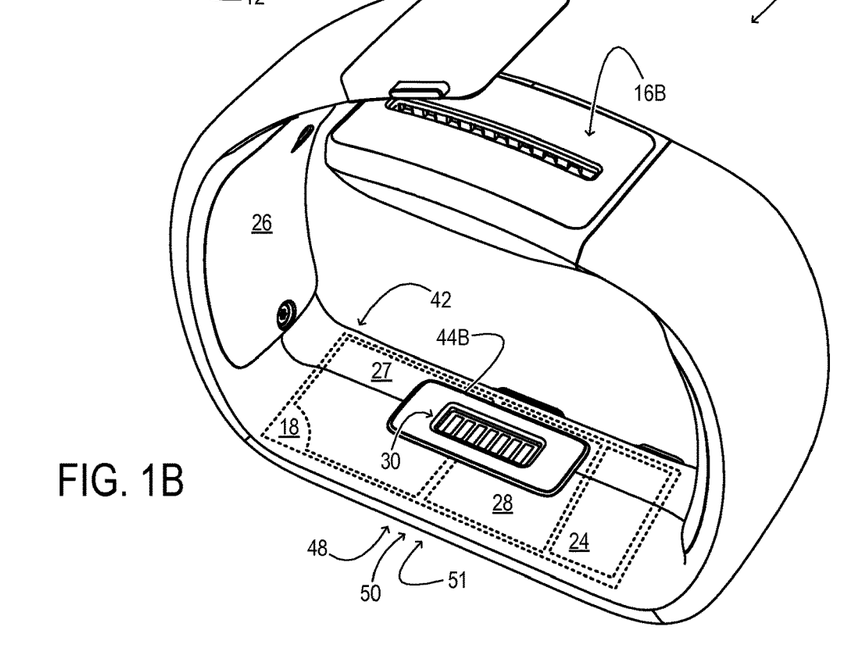

FIGS. 1A and 1B show aspects of an example sensory-and-logic system in the form of a wearable electronic device 10. The illustrated device is band-shaped and may be worn around a wrist. Device 10 includes at least four flexion regions 12 linking less flexible regions 14. The flexion regions of device 10 may be elastomeric in some examples. Fastening componentry 16A and 16B is arranged at both ends of the device. The flexion regions and fastening componentry enable the device to be closed into a loop and to be worn on a user's wrist. In other implementations, wearable electronic devices of a more elongate band shape may be worn around the user's bicep, waist, chest, ankle, leg, head, or other body part. The device, for example, may take the form of eye glasses, a head band, an arm-band, an ankle band, a chest strap, or an implantable device to be implanted in tissue.

Wearable electronic device 10 includes various functional components integrated into regions 14. In particular, the electronic device includes a compute system 18, display 20, loudspeaker 22, communication suite 24, and various sensors. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable electronic device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. Aspects of the compute system are described in further detail with reference to FIG. 6.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable electronic device 10 and other computer systems, as well as providing recharge power. The communication suite may further include two-way Bluetooth, Wi-Fi, cellular, near-field communication and/or other radios. In some implementations, the communication suite may include an additional transceiver for optical, line-of-sight (e.g., infrared) communication.

In wearable electronic device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, etc.

FIGS. 1A and 1B show various other sensors of wearable electronic device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable electronic device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44B in the illustrated configuration is an optical sensor module 46. The optical sensor module may include an optical source configured to illuminate tissue of the user and a matched optical sensor to detect reflected illumination from the tissue of the user. Further details regarding the optical sensor module, optical source, and optical sensor are provided with reference to FIGS. 2A-2C and FIG. 3. Compute system 18 may use input from the contact sensor modules and/or the optical sensor module to assess whether or not the device is being worn, for instance. In some implementations, the input may be used to determine how tightly the wearable electronic device is being worn. The optical sensor module may be used to determine blood flow through the capillaries in the skin and thereby provide a measurement of the wearer's heart rate, blood oxygen level, blood glucose level, and/or other biomarkers with optical properties.

Wearable electronic device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer/caloriecounting function, for example. Data from the accelerometer and gyroscope may be combined with geomagnetic data from the magnetometer to further define the inertial and rotational data in terms of geographic orientation. The wearable electronic device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2A:
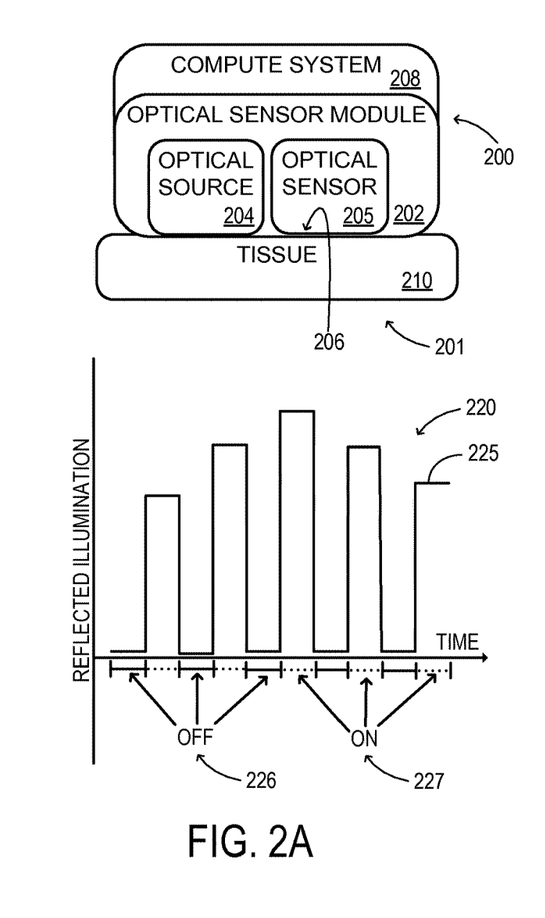
FIGS. 2A, 2B, and 2C schematically show an optical pressure sensor and example data traces output by the optical pressure sensor.
Figure 2B:
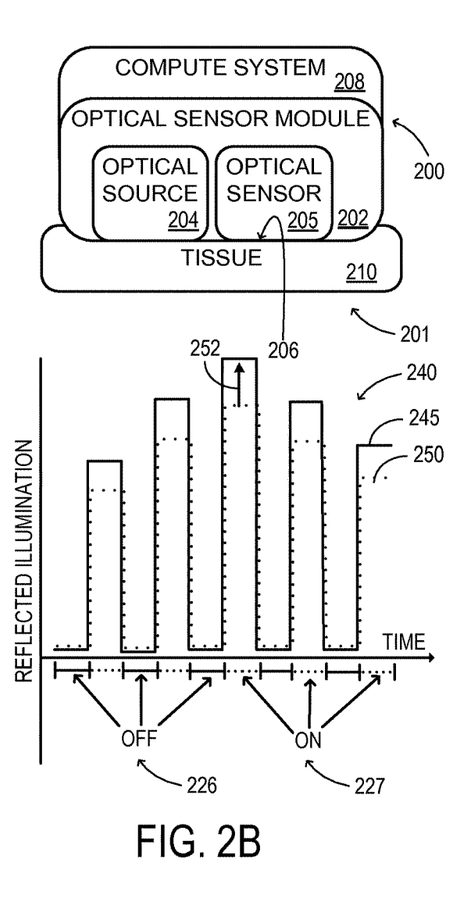
Figure 2C:
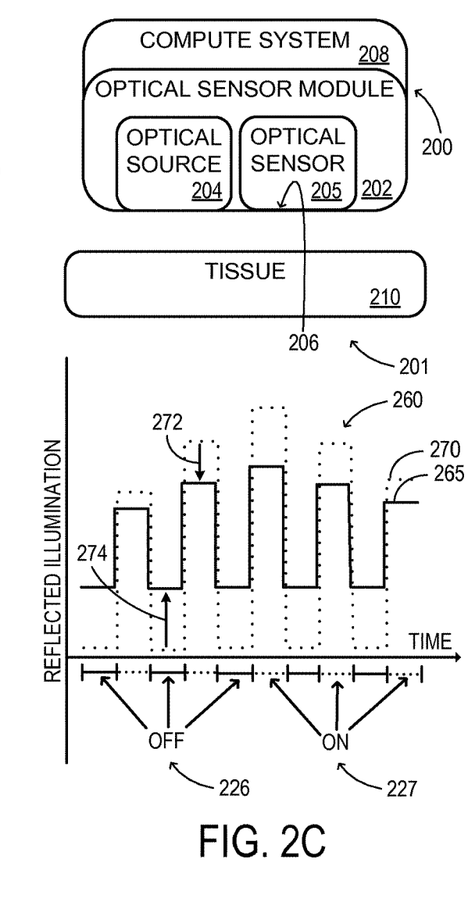

FIGS. 2A-2C show schematic depictions of a sensoryand-logic system 200 coupled to the wrist of a user 201 so that an optical sensor module 202 is adjacent to the tissue 203 of user 201. Optical sensor module 202 comprises an optical source 204 configured to illuminate tissue 203, and an optical sensor 205 configured to measure reflected illumination from the tissue. Optical source 204 may comprise one or more LED emitters, for example, while optical sensor 205 may comprise one or more photodiodes matched to detect light at frequencies based on the frequencies of light output by the optical source. Optical sensor 205 may be configured such that a surface 206 of the optical sensor is in direct contact with the tissue of the user. Surface 206 may comprise an optical filter configured to block, filter, or otherwise limit ambient light from reaching the optical sensor. Sensory-and-logic system 200 may further comprise compute system 208. Compute system 208 may be configured to provide control signals to optical source 204 and optical sensor 205, and to receive an optical signal from optical sensor 205 representing measured illumination. As described further herein, compute system 208 may be configured to process the optical signal to determine a pressure between the surface 206 of the optical sensor and tissue 210, and further configured to utilize the determined pressure in downstream applications.

FIG. 2A shows an example chart 220 for reflected illumination as seen by optical sensor 205. Chart 220 includes plot 225, indicating the amplitude of a signal output by optical sensor 205 to compute system 208 over time. In this example, optical source 204 is configured to pulse on and off. Time periods where optical source 204 is pulsed off are indicated by solid bars at 226. Time periods where optical source 204 is pulsed on are indicated by dashed bars at 227. In this example, the pressure between surface 206 and tissue 210 may be considered a relatively moderate pressure.

During the time periods where optical source 204 is pulsed off, the amount of illumination reflected to optical sensor 205 is relatively low, as shown by plot 225. The illumination measured by optical sensor 205 while optical source 204 is off is due to ambient light transmitted through surface 206. For chart 220, the amount of ambient light transmitted through surface 206 remains relatively constant, as the pressure between surface 206 and tissue 210 remains relatively constant.

During time periods where optical source 204 is pulsed on, the amount of illumination reflected to optical sensor 205 is greater than the amount of illumination reflected to the optical sensor when the optical source is pulsed off. As shown by plot 225, the amount of reflected illumination changes over time, even though the pressure between surface 206 and tissue 210 remains relatively constant. This may be due to some of the light output from optical source 204 reflecting off blood and blood vessels in tissue 210. The movement of blood through the blood vessels causes the blood vessels to expand and contract, thus causing a change in the optical properties of the user's skin. The color of blood also changes across the heart beat cycle, as newly pumped blood contains more oxygen, and thus has a different absorption spectrum than blood exiting the local blood vessels. The repetitive nature of the heart beat yields a periodic plot when illuminated by an optical source. Each successive heart beat yields an amplitude peak. As such, the output of optical sensor 205 may be used to determine a heart rate of the user.

While some of the reflected illumination seen by optical sensor 205 comes from blood, much is reflected by fat and connective tissues. As the upper layers of the skin are compressed, blood is forced out of the skin in the compressed area. As blood is an absorber of green light, the compressed skin thus adsorbs less light and reflects more light. Additionally, more light reaches the highly reflective basal cell layer of tissue 210. This increase in reflectivity causes an increase in total illumination seen by the optical sensor when optical source 204 is pulsed on. The change in reflected illumination is monotonic with pressure, e.g., the harder surface 206 is compressed into tissue 210, the more illumination will be reflected. Thus, after establishing a baseline amount of reflected illumination for a user (which will vary across users as a function of tissue melanin levels, beta carotene levels, freckling, bilirubin levels, etc.), a change in total reflected illumination while optical source 204 is pulsed on can be used to assess changes in pressure between surface 206 and tissue 210. A baseline may be determined over multiple periods of wearing sensory-and-logic system 200. For illustrative purposes, plot 225 will be used as a baseline amount of reflected illumination in FIGS. 2B and 2C, although a mean total internal reflection baseline may be determined over a duration including multiple heart beats. In some applications, a pressure-sensitive resistor or other pressure sensor may be used to establish a baseline.

FIG. 2B schematically shows an example where the pressure between surface 206 and tissue 210 is relatively high. Sensory-and-logic system 200 is shown depressed into tissue 210. FIG. 2B further shows an example chart 240 for reflected illumination output by optical sensor 205 to compute system 208 over time. Chart 240 includes plot 245, indicating the amplitude of a signal output by of optical sensor 205 to compute system 208 over time. Chart 240 further includes plot 250, indicating the amplitude of a baseline (or reference) amount of illumination for optical sensor 205 for a relatively moderate level of pressure between surface 206 and tissue 210.

During the time periods where optical source 204 is pulsed off, the amount of illumination reflected to optical sensor 205 is relatively low, as shown by plot 245. For chart 240, the amount of ambient light transmitted through surface 206 remains relatively constant, as the pressure between surface 206 and tissue 210 remains relatively constant. Further, the amount of illumination indicated by plot 245 during sensor-off periods is similar to the baseline amount of illumination indicated by plot 250. However, during time periods where optical source 204 is pulsed on, the amount of reflected illumination reflected indicated by plot 245 is greater than the baseline amount of illumination indicated by plot 250. This shift is due to a pressure increase and is represented by arrow 252.

Accordingly, compute system 208 may compare the measured reflected illumination to the predetermined baseline optical sensor output corresponding to the user. Further, the compute system may output an increased pressure between the surface of the optical sensor and the tissue responsive to the increase in a ratio of the measured reflected illumination to the predetermined baseline optical sensor output during time periods when the optical source is pulsed on.

FIG. 2C schematically shows an example where the pressure between surface 206 and tissue 210 is relatively low. Sensory-and-logic system 200 is shown as being separated from tissue 210. FIG. 2C further shows an example chart 260 for reflected illumination as seen by optical sensor 205. Chart 260 includes plot 265, indicating the amplitude of a signal output by optical sensor 205 to compute system 208 over time. Chart 260 further includes plot 270, indicating the amplitude of a baseline (or reference) amount of illumination for optical sensor 205 for a relatively moderate level of pressure between surface 206 and tissue 210.

During the time periods where optical source 204 is pulsed on, the amount of illumination reflected to optical sensor 205 as indicated by plot 265 is relatively lower than the baseline amount of reflected illumination. This shift due to a pressure decrease is represented by arrow 272. Accordingly, compute system 208 may output a decreased pressure between the surface of the optical sensor and the tissue responsive to a decrease in a ratio of the measured reflected illumination to the predetermined baseline optical sensor output during time periods when the optical source is pulsed on.

Further, during the time periods where optical source 204 is pulsed off, the amount of illumination reflected to optical sensor 205 as indicated by plot 265 is relatively greater than the baseline amount of reflected illumination. This shift due to a pressure decrease is represented by arrow 274. In this example, the increase in ambient light in conjunction with the decrease in reflected illumination may increase a confidence that the changes in measured reflected illumination are due to a decrease in pressure between surface 206 and tissue 210. However, the ratio of ambient light to reflected illumination may be representative of a change in pressure, a change in ambient lighting conditions, and/or a change in user movement. If the signal from optical sensor 205 shows no or very small changes between pulse-on and pulse-off periods (e.g., the ambient light and reflected illumination are within a threshold), this may be indicative that the sensory and logic system is not being worn by a user (e.g., zero pressure between the optical sensor surface and tissue).

Figure 3:
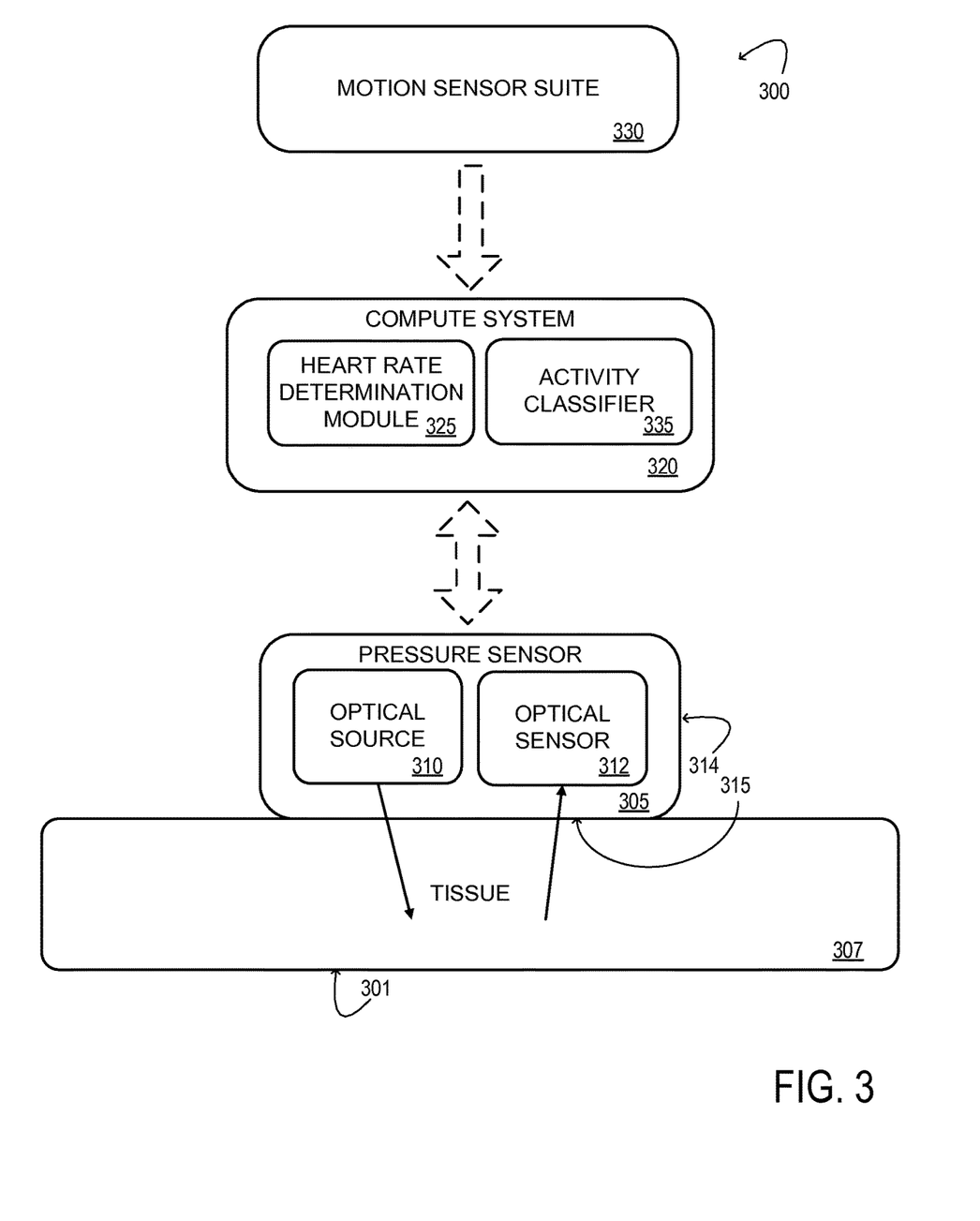
FIG. 3 schematically shows an example wearable electronic device.

FIG. 3 shows a schematic depiction of a sensory-and-logic system 300 coupled to the wrist of a user 301 so that a pressure sensor 305 is adjacent to the tissue 307 of user 301. Pressure sensor 305 comprises an optical source 310 configured to illuminate tissue of the user, and an optical sensor 312, configured to measure reflected illumination from the tissue. Optical source 310 may comprise one or more LED emitters, for example, while optical sensor 312 may comprise one or more photodiodes matched to detect light at frequencies that are based on the frequencies of light output by the optical source (e.g., green light). Pressure sensor 305 may be coupled within a housing 314 configured to promote contact between a surface 315 of pressure sensor 305 and tissue 307, and further configured to block, filter, or otherwise limit ambient light from reaching the optical sensor. For example, surface 315 may comprise a dichroic filter matched to one or more LEDs comprising optical source 310. The dichroic filter may be configured to allow light within a range of the LED wavelength to reach optical sensor 205, as the LED wavelength may fluctuate based on temperature, voltage, etc. For example, the dichroic filter may allow light of +/−20 nm of the LED wavelength to reach optical sensor. Further, the optical sensor may allow some transmission from other wavelengths, such as up to 1.5% of visible, infrared, and/or UV light wavelengths.

Pressure sensor 305 may determine a pressure between surface 315 and tissue 307 based on the measured reflected illumination. The determined pressure, along with raw data representing measured reflected illumination from optical sensor 312 may be provided to compute system 320. In some examples, the pressure may be determined at compute system 320. As described with regard to FIG. 2, the measured reflected illumination may further be used to determine whether a sensory-and-logic system 300 is being worn by a user.

Compute system 320 may provide control signals to optical source 310 and optical sensor 312. For example, optical source 310 may operate in a pulsed-on mode at a pulsation frequency based on control signals received from compute system 320. The pulsation frequency may be predetermined, or may be a function of current operating and ambient conditions (e.g., optical signal quality, user motion as determined by motion sensor suite 330, downstream applications of the optical sensor data, etc.). Compute system 320 may also provide control signals to optical source 310 to vary the intensity of the light output by optical sensor 312. For example, the light intensity may be increased based on an increase in detected ambient light, or decreased based on an increased pressure between surface 315 and tissue 307.

Compute system 320 may comprise a heart rate determination module 325. Heart rate determination module 325 may receive raw signals from optical sensor 312, and may further process the raw signals to determine heart rate, blood oxygen level, etc. The raw signals may be processed through filters to remove noise from the raw signal. For example, user motion may contribute to the moving of fluid through and near blood vessels that may not be discernible from blood flow driven by heart beats. The motion may be filtered out of the raw optical signal based on motion signals received from motion sensor suite 330. Processed signals may be stored and output via compute system 320. Control signals sent to optical source 310 and optical sensor 312 may be based on signals received from optical sensor 312, one or more motion sensors comprising motion sensor suite 330, ambient light sensors, information stored in compute system 320, input signals, etc.

By coupling pressure sensor 305 to tissue 307, the majority of light reaching optical sensor 312 may be light originating from optical source 310 that has reflected off tissue 307. As an example, FIG. 1A shows a wearable electronic device 10 that is configured to position optical sensor module 46 such that its optical source may illuminate capillaries located beneath the skin of the user's forearm while the wearable electronic device is worn by the user. In other configurations, an optical sensor module may be positioned within a wearable electronic device such that an optical source illuminates a radial artery through the skin of the user while the wearable electronic device is worn by the user.

An optical sensor module and its associated heart rate determination module may be housed separately and configured to communicate via a communication suite. For example, an optical sensor module may be included in a head set and configured to illuminate capillaries located in the user's ear lobe while the head set is worn by the user. The associated heart rate determination module may reside in a wrist-worn computing device configured to communicate with the head set, via wireless communication, for example. An optical sensor may be configured to sense light reflected off of blood vessels located beneath the skin of the user (e.g., wrist worn), or the optical sensor may be configured to sense light transmitted through blood vessels located beneath the skin of the user (e.g., ear worn). If optical sensor 312 is operated in a continuously-on mode while optical source 310 is pulsed on and off, optical sensor 312 will detect ambient light when optical source is off. The ambient light detected may be subtracted from, or otherwise used to smooth the raw signal from optical sensor 312.

Figure 4:
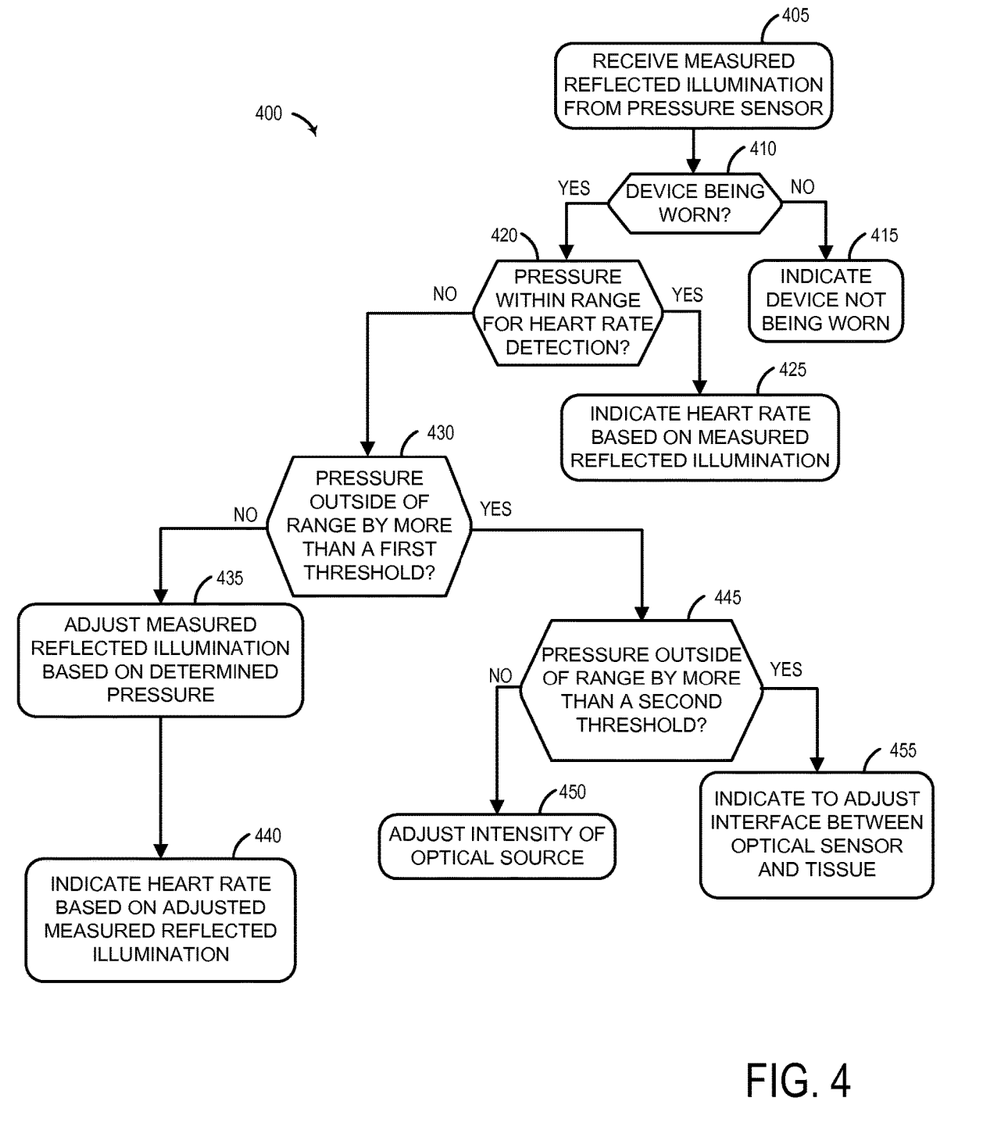
FIG. 4 shows an example method for determining a heart rate based on the output of an optical pressure sensor.

The determined pressure between surface 315 and tissue 307 may be used to filter raw data output from optical sensor 312 prior to determining heart rates. FIG. 4 shows an example method 400 for determining a heart rate based on the output of an optical pressure sensor. At 405, method 400 may include receiving measured reflected illumination from the optical pressure sensor. This may further include determining a pressure at a surface of the optical sensor, or receiving a determined pressure at the surface of the optical sensor. Continuing at 410, method 400 may include determining whether the device comprising the optical pressure sensor is being worn by a user. As described herein with regard to FIG. 2, this may include assessing whether the optical pressure sensor is being worn based on the measured illumination during time periods when the optical source is pulsed off (e.g., an increase in ambient light). The measured reflected illumination during time periods when the optical source is pulsed off may also be compared to the measured reflected illumination when the optical source is pulsed on. If it is determined that the device comprising the optical pressure sensor is not being worn by a user, method 400 may proceed to 415. At 415, method 400 may include indicating that the device is not being worn. This may include adjusting one or more operating parameters of the device, for example, shutting down hardware and logic configured to function when the device is being worn.

If it is determined that the device comprising the optical pressure sensor is being worn by a user, method 400 may proceed to 420. At 420, method 400 may include determining whether the pressure at the surface of the optical sensor is within a predetermined range for detecting the heart rate of a user without adjusting for the determined pressure. If the determined pressure is within the range, method 400 may proceed to 425. At 425, method 400 may include indicating a heart rate of the user based on the measured reflected illumination.

If the determined pressure is outside the range for detecting the heart rate of a user without adjusting for the pressure, method 400 may proceed to 430. At 430, method 400 may include determining whether the determined pressure is outside the predetermined range by more than a first threshold. The first threshold may represent a pressure range (both above and below the predetermined range) where the measured reflected illumination may be adjusted to yield an accurate heart rate. If the determined pressure is not outside the predetermined range by more than the first threshold, method 400 may proceed to 435. At 435, method 400 may include adjusting the measured reflected illumination based on the determined pressure. For example, a filter may be applied to the measured reflected illumination based on the determined pressure. Continuing at 440, method 400 may include indicating a heart rate of the user based on the adjusted measured reflected illumination.

If the determined pressure is outside the predetermined range by more than the first threshold, method 400 may proceed to 445. At 445, method 400 may include determining whether the determined pressure is outside the predetermined range by more than a second threshold, greater than the first threshold. The second threshold may represent a pressure range (both above and below the predetermined range) where the intensity of the optical source may be adjusted and still yield an accurate heart rate. If the determined pressure is not outside the predetermined range by more than the second threshold, method 400 may proceed to 450. At 450, method 400 may include adjusting the intensity of the optical source. For example, if the determined pressure is above the predetermined range, the intensity of the optical source may be decreased. If the determined pressure is below the predetermined range, the intensity of the optical source may be increased.

If the determined pressure is outside the predetermined range by more than the second threshold, method 400 may proceed to 455. At 455, method 400 may include indicating to the user to adjust the interface between the surface of the optical sensor and the underlying tissue.

Returning to FIG. 3, compute system 320 may further comprise an activity classifier 335. Activity classifier 335 may be trained to recognize if the user is actively engaged in a physical activity during a time period. In general, activity classifier 335 may be trained through a machine-learning process to recognize signal characteristics that are representative of a user being actively engaged in a physical activity or exercise and/or to recognize signal characteristics that are representative of a user not being actively engaged in a physical activity or exercise. Activity classifier 335 may be trained through a machine-learning process to further recognize signal characteristics that are representative of a user being actively engaged in a particular one of a plurality of specific physical activities or exercises, as well as recognizing predetermined signal characteristics that are representative of a user not being actively engaged in a particular one of a plurality of specific physical activities or exercises. For example, activity classifier 335 may utilize a support vector machine (SVM), such as a linear support vector machine. In some examples, activity classifier 335 may utilize a machine-learning decision tree or a forest of decision trees.

In some examples where activity classifier 335 utilizes an SVM, the SVM may be configured to generate a vector of numbers, and further configured to multiply the predetermined signal characteristics by the vector of numbers to obtain a plurality of multiplication products. The SVM may be further configured to compare the multiplication products to a threshold or thresholds determined through machine learning. The SVM may then be configured to classify a value above the threshold as representative of a time period wherein the user is actively engaged in a physical activity and classify a value below the threshold as representative of a time period wherein the user is not actively engaged in a physical activity. Similarly, the SVM may generate a plurality of vectors of numbers for each of the plurality of specific physical activities or exercises, and multiply the predetermined signal characteristics by the plurality of vectors of numbers. The resulting multiplication products may then be compared to thresholds for each of the plurality of specific physical activities of exercises to determine whether the signal characteristics are representative of a specific physical activity or exercise during the time period.

User motion may influence the pressure between surface 315 and tissue 307. For example, when sensory and logic system is incorporated into a wristworn device, pressure between surface 315 and tissue 307 will increase due to forearm contraction and extension. Repetitive exercises such as push-ups, pull-ups, bicep curls, etc., may yield characteristic pressure signals indicative of that exercise. The determined pressure between surface 315 and tissue 307 over time may thus be provided as input signals to activity classifier 335. For example, activity classifier 335 may compare the determined pressure over time to pressure data sets representative of each of a plurality of predetermined activities, and classifying the determined pressure as representative of a type of predetermined activity based on the comparison of the determined pressure to the pressure data sets.

Signals from one or more motion sensors comprising motion sensor suite 330 may also be provided as input signals to activity classifier 335. For example, activity classifier 335 may receive a signal from one or more motion sensors indicating movement over time. Activity classifier 335 may then compare the indicated movement over time to movement data sets representative of each of a plurality of predetermined activities, and classify the indicated movement as representative of a type of predetermined activity based on the comparison of the indicated movement to the movement data sets.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 5.

Figure 5:
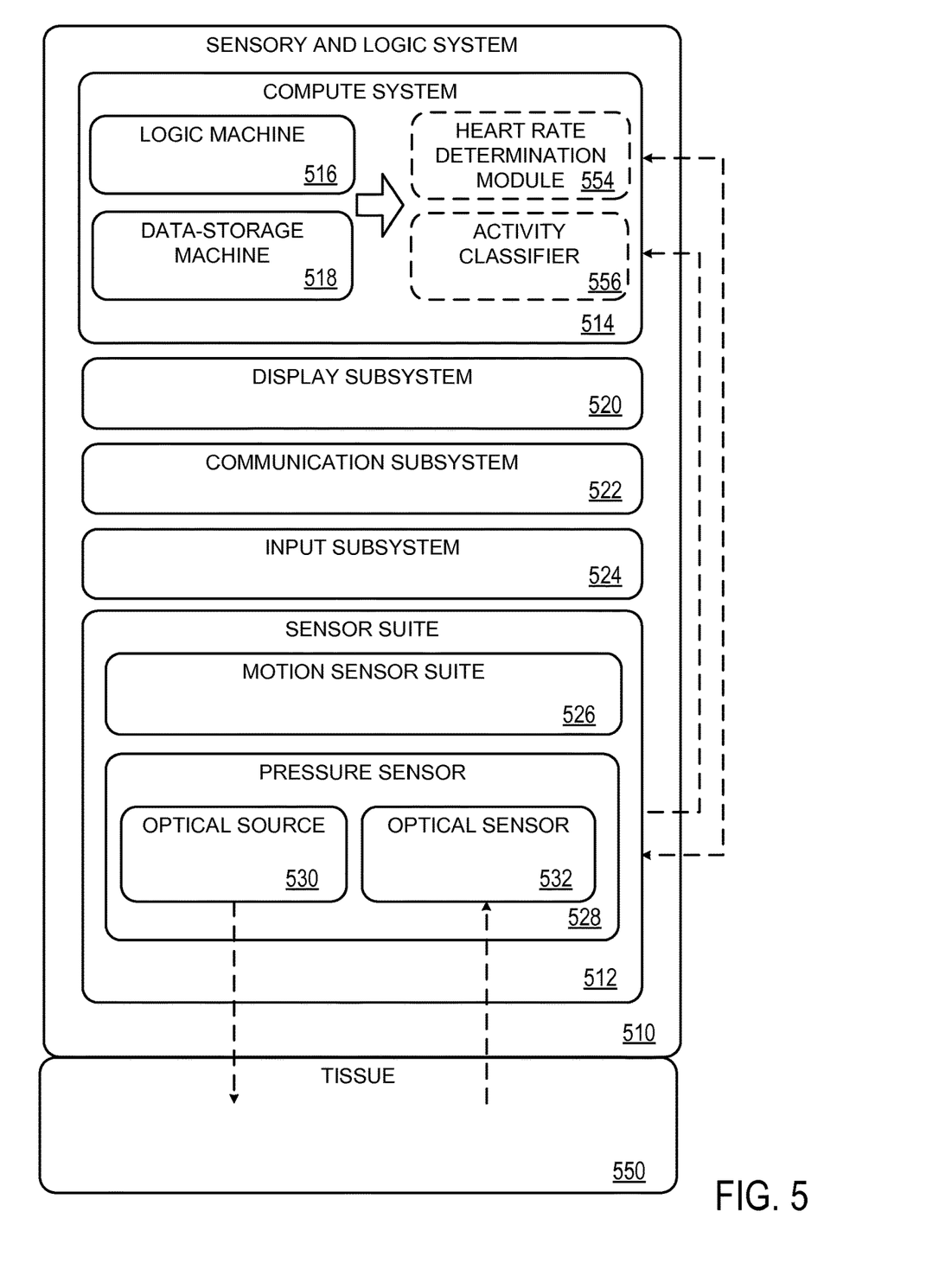
FIG. 5 schematically shows a sensory-and-logic system useable to characterize biometrics of a user based on the output of an optical pressure sensor.

FIG. 5 schematically shows a form-agnostic sensory-and-logic system 510 that includes a sensor suite 512 operatively coupled to a compute system 514. The compute system includes a logic machine 516 and a data-storage machine 518. The compute system is operatively coupled to a display subsystem 520, a communication subsystem 522, an input subsystem 524, and/or other components not shown in FIG. 5.

Logic machine 516 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 516 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 518 includes one or more physical devices configured to hold instructions executable by logic machine 516 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 518 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 516 and data-storage machine 518 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 520 may be used to present a visual representation of data held by data-storage machine 518. This visual representation may take the form of a graphical user interface (GUI). As the herein described methods and processes change the data held by the storage machine, and thus transform the state of the storage machine, the state of display subsystem 520 may likewise be transformed to visually represent changes in the underlying data. Display subsystem 520 may include one or more display subsystem devices utilizing virtually any type of technology. Such display subsystem devices may be combined with logic machine 516 and/or data-storage machine 518 in a shared enclosure, or such display subsystem devices may be peripheral display subsystem devices. Display 20 of FIGS. 1A and 1B is an example of display subsystem 520.

Communication subsystem 522 may be configured to communicatively couple compute system 514 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 522.

Input subsystem 524 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 524.

Sensor suite 512 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIGS. 1A and 1B. Sensor suite 512 may include motion sensor suite 526. Motion sensor suite 526 may include one or more of an accelerometer, gyroscope, magnetometer, or other suitable motion detectors. Sensor suite 512 may further include pressure sensor 528. As described herein, pressure sensor 528 may include optical source 530 and optical sensor 532. Optical source 530 may comprise one or more LED emitters, for example, while optical sensor 532 may comprise one or more photodiodes matched to detect light at frequencies that are based on the frequencies of light output by the optical source. Optical source 530 may be configured to illuminate tissue 550, and optical sensor 532 may be configured to measure illumination reflected from or transmitted through tissue 550.

Compute system 514 may include heart rate determination module 554, which may be communicatively coupled to logic machine 516 and data-storage machine 518. Heart rate determination module 554 may receive raw signals from optical sensor 532, and may further process the raw signals to determine heart rate, caloric expenditures, etc. Processed signals may be stored and output via compute system 514. Control signals sent to optical source 530 and optical sensor 532 may be based on signals received from optical sensor 532, signals derived from sensor suite 512, information stored in data-storage machine 518, input received from communication subsystem 522, input received from input subsystem 524, etc.

Compute system 514 may further include activity classifier 556, which may be communicatively coupled to logic machine 516 and data-storage machine 518. Activity classifier 556 may receive raw signals from optical sensor 532, processed signals from pressure sensor 528 and raw or processed signals from motion sensor suite 526 and/or other sensors. Activity classifier 556 may process the raw or processed signals and classify the signals as characteristic of one or more of a plurality of predetermined activities. Classified activity may be stored and output via compute system 514.

The configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A pressure sensor, comprising:
an optical source configured to output light to illuminate tissue of a user;
an optical sensor configured to measure reflected illumination from the tissue; and
a compute machine configured to:
output a pressure between a surface of the optical sensor and the tissue, the pressure determined as a function of the measured reflected illumination;
based on the output pressure being outside a range for heart rate detection by less than a first threshold, adjust the measured reflected illumination, and output a heart rate based on the adjusted measured reflected illumination; and
dynamically adjust an intensity of the light output by the optical source based on the output pressure being outside the range for the heart rate detection by more than the first threshold but less than a second threshold.

2. The pressure sensor of claim 1, where the optical source is configured to pulse on and off.

3. The pressure sensor of claim 2, where the compute machine is configured to:
compare the measured reflected illumination to a predetermined baseline optical sensor output corresponding to the user; and
output an increased pressure between the surface of the optical sensor and the tissue responsive to an increase in a ratio of the measured reflected illumination to the predetermined baseline optical sensor output during time periods when the optical source is pulsed on.

4. The pressure sensor of claim 2, where the compute machine is configured to:
indicate whether the pressure sensor is being worn based on the measured reflected illumination during time periods when the optical source is pulsed off.

5. The pressure sensor of claim 1, where the compute machine is configured to:
indicate to the user to adjust an interface between the surface of the optical sensor and the tissue based on the output pressure.

6. The pressure sensor of claim 1, where the compute machine is configured to:
based on the output pressure being within the range for the heart rate detection, output a heart rate of the user based on the measured reflected illumination.

7. The pressure sensor of claim 1, where the compute machine is configured to:
classify the output pressure as representative of a type of predetermined activity.

8. The pressure sensor of claim 7, further comprising a motion sensor configured to determine movement of the pressure sensor over time, and where the compute machine is further configured to:
classify the determined movement as representative of a type of predetermined activity.

9. The pressure sensor of claim 1, wherein dynamically adjusting the intensity of the light output by the optical source based on the output pressure being outside the range for the heart rate detection further comprises:
increasing the intensity of the light output by the optical source based on the output pressure being below the range for the heart rate detection; and
decreasing the intensity of the light output by the optical source based on the output pressure being above the range for the heart rate detection.

10. A wearable computing device, comprising:
a pressure sensor configured to determine a pressure between a surface of the pressure sensor and tissue of a user over time, the pressure sensor comprising:
an optical source configured to illuminate the tissue of the user; and
and optical sensor configured to measure reflected illumination from the tissue;
a logic machine; and
a data-storage machine holding instructions executable by the logic machine to:
based on a determined pressure being within a pressure range, output a heart rate based on the measured reflected illumination;
based on the determined pressure being outside the pressure range by less than a first threshold, adjust the measured reflected illumination, and output a heart rate based on the adjusted measured reflected illumination; and
based on the determined pressure being outside the pressure range by more than the first threshold but less than a second threshold which is greater than the first threshold, adjust an intensity of light output by the optical source.

11. The device of claim 10, where the optical source is configured to pulse on and off, and wherein the data-storage machine further holds instructions executable by the logic machine to:
compare the measured reflected illumination to a predetermined baseline optical sensor output corresponding to the user; and
output an increased pressure between the surface of the optical sensor and the tissue responsive to an increase in a ratio of the measured reflected illumination to the predetermined baseline optical sensor output during time periods when the optical source is pulsed on.

12. The device of claim 11, where the pressure sensor is further configured to:
indicate whether the pressure sensor is being worn based on the measured reflected illumination during time periods when the optical source is pulsed off.

13. The device of claim 10, where the data-storage machine further holds instructions executable by the logic machine to:
indicate to the user to adjust an interface between the surface of the pressure sensor and the user's tissue based on the determined pressure being outside the pressure range by more than the second threshold.

14. A wearable computing device, comprising:
an optical source configured to illuminate tissue of a user and to pulse on and off;
an optical sensor configured to measure reflected illumination from the tissue; and
a compute system configured to:
establish a baseline optical sensor output for the user over time based on an output of the optical sensor over a duration including multiple on-and-off pulsations of the optical source;
compare the measured reflected illumination to the baseline optical sensor output;
output a heart rate based on the measured reflected illumination and the baseline optical sensor output;
output a pressure between a surface of the optical sensor and the tissue based on the measured reflected illumination and the baseline optical sensor output;
based on the output pressure being outside a range for heart rate detection by less than a first threshold, adjust the measured reflected illumination, and output the heart rate based on the adjusted measured reflected illumination; and
dynamically adjust an intensity of the light output by the optical source based on the output pressure being outside the range for the heart rate detection by more the first threshold but less than a second threshold.

* * * * *